(12) United States Patent
Oosake

(10) Patent No.: US 11,605,363 B2
(45) Date of Patent: Mar. 14, 2023

(54) MEDICAL IMAGE PROCESSING APPARATUS FOR REDUCING EXAMINATION LOAD

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 32 days.

(21) Appl. No.: 17/129,864

(22) Filed: Dec. 21, 2020

(65) Prior Publication Data

US 2021/0110915 A1 Apr. 15, 2021

Related U.S. Application Data

(63) Continuation of application No. PCT/JP2019/022047, filed on Jun. 3, 2019.

(30) Foreign Application Priority Data

Jul. 27, 2018 (JP) .............................. JP2018-140953

(51) Int. Cl.
*G09G 5/14* (2006.01)
*G16H 30/40* (2018.01)
(Continued)

(52) U.S. Cl.
CPC ......... *G09G 5/14* (2013.01); *A61B 1/000094* (2022.02); *G06T 7/0012* (2013.01);
(Continued)

(58) Field of Classification Search
CPC ................ A61B 1/045; A61B 1/00055; A61B 1/0005; G06T 2207/30004; G06T 7/0012
See application file for complete search history.

(56) References Cited

U.S. PATENT DOCUMENTS 8,758,337 B2 * 6/2014 Skwarek ............ A61B 18/1206
606/34
2011/0254937 A1 10/2011 Yoshino
(Continued)

FOREIGN PATENT DOCUMENTS

| JP | 2011160848 | 8/2011 |
|----|------------|--------|
| JP | 2013135776 | 7/2013 |
| WO | 2017081976 | 5/2017 |

OTHER PUBLICATIONS

"Search Report of Europe Counterpart Application", dated Oct. 14, 2021, p. 1-p. 7.
(Continued)

*Primary Examiner* — Weiming He
(74) *Attorney, Agent, or Firm* — JCIPRNET

(57) ABSTRACT

A bar is displayed in a second region. Display of the bar starts in a longest state when an undetected state in which a region of interest is not detected transitions to a detected state in which the region of interest is detected, and display in the longest state is maintained until the detected state transitions to the undetected state. When the detected state transitions to the undetected state, the bar is reduced in length over time. When a predetermined time elapses, the length of the bar becomes 0, and the bar disappears. In addition, in a case where the undetected state transitions to the detected state before the bar disappears, the length of the bar returns to the longest.

11 Claims, 10 Drawing Sheets

(51) Int. Cl.
*G06T 7/00* (2017.01)
*G09G 5/37* (2006.01)
*G06V 10/25* (2022.01)
*A61B 1/00* (2006.01)

(52) U.S. Cl.
CPC ............... *G06V 10/25* (2022.01); *G09G 5/37* (2013.01); *G16H 30/40* (2018.01); *G06T 2207/30004* (2013.01); *G06V 2201/03* (2022.01); *G09G 2354/00* (2013.01); *G09G 2380/08* (2013.01)

(56) References Cited

U.S. PATENT DOCUMENTS

| | | | | |
|---|---|---|---|---|
| 2012/0274754 | A1* | 11/2012 | Tsuruoka | A61B 1/0638 348/222.1 |
| 2016/0191818 | A1* | 6/2016 | Matsushima | H04N 5/232939 386/224 |
| 2018/0249900 | A1 | 9/2018 | Imaizumi et al. | |
| 2018/0358124 | A1* | 12/2018 | Scheuer | G16H 10/65 |

OTHER PUBLICATIONS

"International Search Report (Form PCT/ISA/210) of PCT/JP2019/022047," dated Aug. 20, 2019, with English translation thereof, pp. 1-3.
"Written Opinion of the International Searching Authority (Form PCT/ISA/237) of PCT/JP2019/022047," dated Aug. 20, 2019, with English translation thereof, pp. 1-14.

* cited by examiner

MEDICAL IMAGE PROCESSING APPARATUS FOR REDUCING EXAMINATION LOAD

CROSS-REFERENCE TO RELATED APPLICATIONS

This application is a Continuation of PCT International Application No. PCT/JP2019/022047 filed on 3 Jun. 2019, which claims priority under 35 U.S.C. § 119(a) to Japanese Patent Application No. 2018-140953 filed on 27 Jul. 2018. The above application is hereby expressly incorporated by reference, in its entirety, into the present application.

BACKGROUND OF THE INVENTION

1. Field of the Invention

The present invention relates to a medical image processing apparatus using an analysis result of a medical image.

2. Description of the Related Art

In the medical field, by using a medical image such as an endoscopic image, an X-ray image, a computed tomography (CT) image, or a magnetic resonance (MR) image, image diagnosis such as diagnosis of a patient's condition or follow-up is made. On the basis of such image diagnosis, physicians or the like determine a treatment policy or the like.

In recent years, in image diagnosis using a medical image, automatic recognition processing is being performed on a region of interest to be observed with attention to a lesion, a tumor, or the like in an organ by a medical image processing apparatus analyzing a medical image. In particular, through machine learning such as deep learning, information about the region of interest is leaned from previous medical images, and the medical image processing apparatus performs recognition processing on a region of interest on the basis of the information acquired through learning, with dramatically high accuracy.

For example, JP2011-160848A (corresponding to US2012/0274754A1) describes an endoscope (medical image processing apparatus) that displays an alert if a region of interest is detected. JP2011-160848A also describes a configuration that continues displaying the alert even if the region of interest becomes out of a screen.

SUMMARY OF THE INVENTION

However, the apparatus described in JP2011-160848A above has a problem of a large examination load. That is, since the apparatus described in JP2011-160848A cannot grasp the elapsed time after change of a detection state of the region of interest (e.g., whether the detection state is a detected state in which the region of interest is detected or an undetected state in which the region of interest is not detected), if the detection state enters the undetected state as a result of the region of interest becoming out of the screen, for example, it is uncertain how much an endoscope is to be moved back in order to enter the detected state by returning the region of interest to the inside of the screen. This increases the load for returning the region of interest to the inside of the screen to enter (make transition to) the detected state again from the undetected state.

The present invention has been made in view of the above background, and an object thereof is to provide a medical image processing apparatus that can reduce the examination load.

In order to solve the above problem, a medical image processing apparatus according to the present invention includes:

a medical image acquiring unit that acquires a medical image obtained by capturing an image of an observation target;

a region-of-interest detecting unit that detects a region of interest from the medical image; and a display control unit that causes a display unit to display report information and the medical image, the report information reporting that the region of interest has been detected, in which the display control unit changes a display manner of the report information by using a detection state of the region of interest and an elapsed time after change of the detection state.

The display control unit may change the display manner of the report information by referring to an elapsed time after the detection state of the region of interest has transitioned from a detected state in which the region of interest is detected to an undetected state in which the region of interest is not detected.

If the detection state of the region of interest transitions from an undetected state in which the region of interest is not detected to a detected state in which the region of interest is detected, the display control unit may cause the display unit to display the report information in a first display manner, and, if the detection state of the region of interest transitions from the detected state to the undetected state, the display control unit may cause the display unit to display the report information in a second display manner.

While the detection state of the region of interest is a detected state in which the region of interest is detected, the region of interest may be displayed to be superposed on the medical image.

The display control unit may cause the display unit to display the elapsed time as the report information, the elapsed time being a time after the detection state of the region of interest has transitioned from the detected state to the undetected state.

The report information may be displayed in a form of a circular or linear time bar that changes in length in accordance with the elapsed time.

The report information may be displayed in a form of a character or a numeral indicative of the elapsed time.

The report information may be displayed in a form of changing a hue or a density in accordance with the elapsed time.

In a screen of the display unit, a first region displaying the medical image and a second region displaying the report information may be provided.

The second region may be provided in a peripheral part of the first region.

In a detected state in which the region of interest is detected, the display control unit may indicate a detected location of the region of interest in the medical image by the display manner of the report information.

In an undetected state in which the region of interest is not detected, the display control unit may indicate a most recent detected location of the region of interest by the display manner of the report information.

The display control unit may indicate the detected location by a display position of the report information.

According to the present invention, since it is possible to grasp the elapsed time after change of the detection state of the region of interest, the examination load can be reduced.

BRIEF DESCRIPTION OF THE DRAWINGS

FIG. 1 is a block diagram illustrating a medical image processing apparatus, an endoscope apparatus, and the like;

DESCRIPTION OF THE PREFERRED EMBODIMENTS

Figure 1:
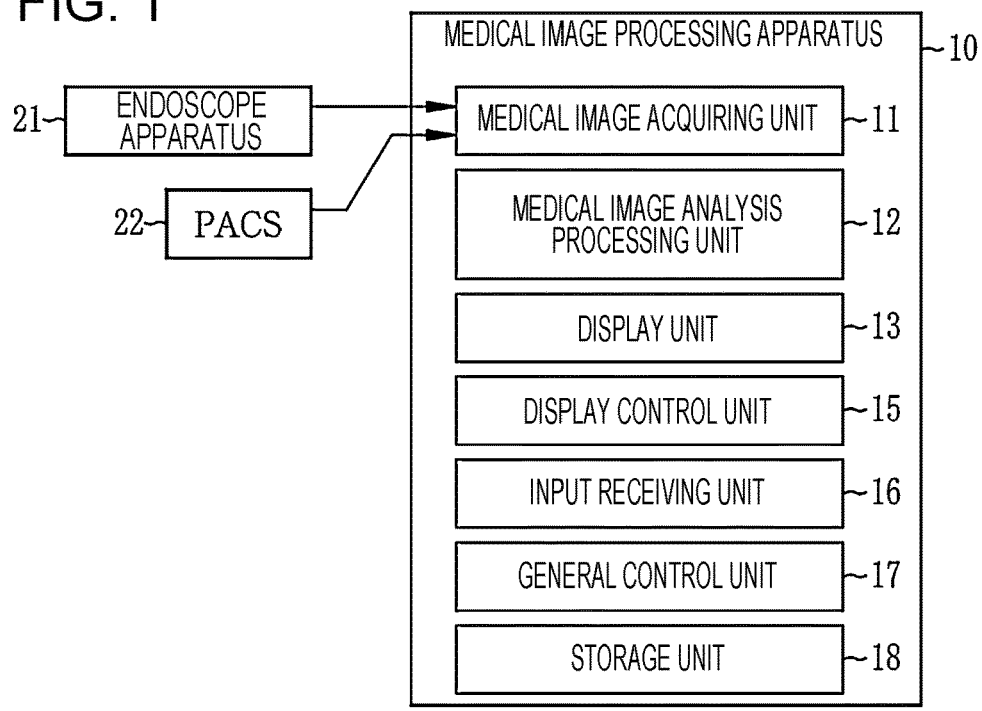

As illustrated in FIG. 1, a medical image processing apparatus 10 includes a medical image acquiring unit 11, a medical image analysis processing unit 12, a display unit 13, a display control unit 15, an input receiving unit 16, a general control unit 17, and a storage unit 18.

The medical image acquiring unit 11 acquires a medical image including a photographic subject image directly from an endoscope apparatus 21 or the like or through a management system or another information system, such as a picture archiving and communication system (PACS) 22. The medical image is a still image or a moving image (so-called examination moving image). In a case where the medical image is a moving image, the medical image acquiring unit 11 can acquire frame images constituting the moving image as still images after examination. In addition, in a case where the medical image is a moving image, display of the medical image includes, not only displaying one typical frame still image constituting the moving image, but also reproducing the moving image once or a plurality of times. In addition, the medical image acquired by the medical image acquiring unit 11 includes, not only an image captured by a physician with a medical apparatus such as the endoscope apparatus 21, but also an image automatically captured by a medical apparatus such as the endoscope apparatus 21 regardless of an image pickup instruction from a physician. Note that both the medical image processing apparatus 10 and the endoscope apparatus 21 perform image processing by using a medical image in this embodiment, and thus, each of the medical image processing apparatus 10 and the endoscope apparatus 21 corresponds to a medical image processing apparatus according to the present invention.

In a case where a plurality of medical images may be acquired, the medical image acquiring unit 11 can selectively acquire one or more medical images from these medical images. In addition, the medical image acquiring unit 11 can acquire a plurality of medical images acquired in a plurality of mutually different examinations. For example, either or both of a medical image acquired in a previously performed examination and a medical image acquired in the most recent examination can be acquired. That is, the medical image acquiring unit 11 can acquire a medical image or medical images as appropriate.

In this embodiment, a plurality of medical images including a photographic subject image are acquired. More specifically, in a case of acquiring a plurality of medical images captured in a single specific examination, the plurality of medical images are acquired from a series of medical images. In addition, in this embodiment, the medical image processing apparatus 10 is connected to the endoscope apparatus 21 and acquires the medical images from the endoscope apparatus 21. That is, the medical images in this embodiment are endoscopic images.

The display unit 13 is a display that displays the medical images acquired by the medical image acquiring unit 11 and an analysis result of the medical image analysis processing unit 12. A monitor or a display included in a device or the like to which the medical image processing apparatus 10 is connected may be shared and used as the display unit 13 of the medical image processing apparatus 10. The manner of the display unit 13 displaying the medical images and the analysis result is controlled by the display control unit 15.

The input receiving unit 16 receives inputs from a mouse, a keyboard, or other operation devices connected to the medical image processing apparatus 10. Operations of the units of the medical image processing apparatus 10 can be controlled by using these operation devices.

The general control unit 17 generally controls the operations of the units of the medical image processing apparatus 10. In a case where the input receiving unit 16 receives an operation input using an operation device, in accordance with the operation input, the general control unit 17 controls the units of the medical image processing apparatus 10.

The storage unit 18 stores a still image of the medical image or the like in a storage device (not illustrated) such as a memory included in the medical image processing apparatus 10 or a storage device (not illustrated) included in a medical apparatus such as the endoscope apparatus 21 or the PACS 22.

Figure 2:
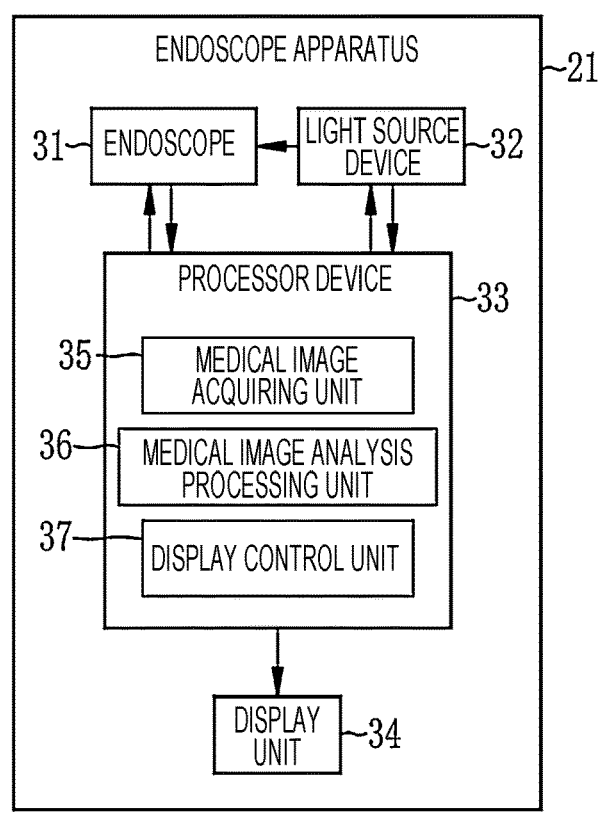
FIG. 2 is a block diagram illustrating the endoscope apparatus.

As illustrated in FIG. 2, the endoscope apparatus 21 to which the medical image processing apparatus 10 is connected in this embodiment has an endoscope 31, a light source device 32, a processor device 33, and a display unit 34. The endoscope 31 acquires an image by capturing an image of a photographic subject irradiated with at least any of light of a white wavelength range or light of a particular wavelength range. The light source device 32 irradiates the inside of the photographic subject with illumination light through the endoscope 31. The display unit 34 displays an endoscopic image captured with the endoscope 31 or the like. The light of the particular wavelength range used by the endoscope 31 as illumination light is, for example, light of a shorter-wavelength range than a green wavelength range, and is, in particular, light of a visible wavelength range of blue or violet.

The processor device 33 includes a medical image acquiring unit 35, a medical image analysis processing unit 36, and a display control unit 37. The medical image acquiring unit 35 acquires a medical image output from the endoscope 31. The medical image analysis processing unit 36 performs analysis processing on the medical image acquired by the medical image acquiring unit 35. Details of processing performed in the medical image analysis processing unit 36 are substantially the same as details of processing performed in the medical image analysis processing unit 12 of the medical image processing apparatus 10. The display control unit 37 causes the display unit 34 to display a medical image obtained by the medical image analysis processing unit 36. The processor device 33 is connected to the medical image processing apparatus 10. Note that the display unit 34 is equivalent to the display unit 13, the medical image acquiring unit 35 is substantially the same as the medical image acquiring unit 11, the medical image analysis processing unit 36 is substantially the same as the medical image analysis processing unit 12, and the display control unit 37 is substantially the same as the display control unit 15.

Figure 3:
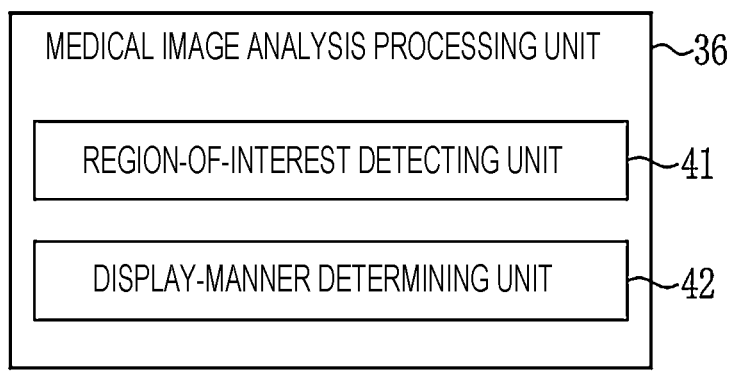
FIG. 3 is a block diagram illustrating functions of a medical image analysis processing unit.

The medical image analysis processing unit 36 performs analysis processing by using the medical image acquired by the medical image acquiring unit 35. As illustrated in FIG. 3, the medical image analysis processing unit 36 includes a region-of-interest detecting unit 41 and a display-manner determining unit 42. The region-of-interest detecting unit 41 performs region-of-interest detection processing for detecting a region of interest 47 (see FIG. 4 to FIG. 6, FIG. 16, FIG. 17, and FIG. 20) from the medical image. As the region-of-interest detection processing, for example, a neural network (NN), a convolutional neural network (CNN), AdaBoost, a random forest, or the like may be employed. In addition, as the region-of-interest detection processing, the region of interest 47 may be detected on the basis of a feature quantity obtained as color information of a medical image, a gradient of a pixel value, or the like. Note that the gradient of the pixel value or the like changes depending on, for example, the shape of the photographic subject (e.g., global ups and downs or local depression or projection in a mucous membrane), color (color of, for example, inflammation, bleeding, redness, or whitening due to atrophy), feature of an organ (e.g., blood vessel thickness, depth, density, or a combination thereof), feature of a structure (e.g., pit pattern), or the like.

Note that the region of interest 47 detected by the region-of-interest detecting unit 41 is a region including, for example, a lesion part typified by a cancer, a benign tumor part, an inflammation part (including, not only a so-called inflammation, but also a part with a change such as bleeding or atrophy), a marking part marked by cauterization by heating or colored with a colorant, a fluorescent agent, or the like, and a biopsy performing part where a biopsy is performed. That is, the region of interest 47 may be a region including a lesion, a region that may possibly be a lesion, a region subjected to certain treatment including a biopsy, a treatment tool including a clip or forceps, a region that needs close observation, regardless of the possibility of a lesion, such as a dark region (a region behind a fold or depth of a luminal organ where observation light is difficult to be delivered), or the like. In the endoscope apparatus 21, the region-of-interest detecting unit 41 detects, as the region of interest 47, a region including at least any of the lesion part, the benign tumor part, the inflammation part, the marking part, or the biopsy performing part.

The display-manner determining unit 42 determines a display manner of report information for reporting that the region of interest 47 has been detected, and also determines a display manner of a medical image 43 (see FIG. 4 to FIG. 17). In accordance with the determined display manners, the display control unit 37 causes the display unit 34 to display the report information and the medical image 43.

Figure 4:
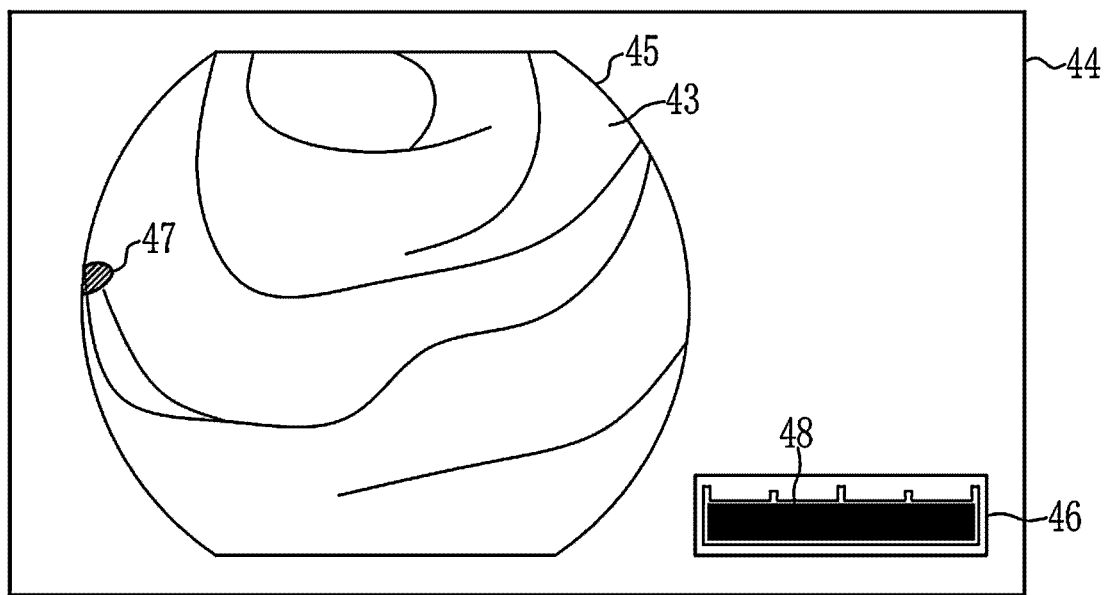
FIG. 4 is an explanatory diagram illustrating a display manner of report information.
Figure 5:
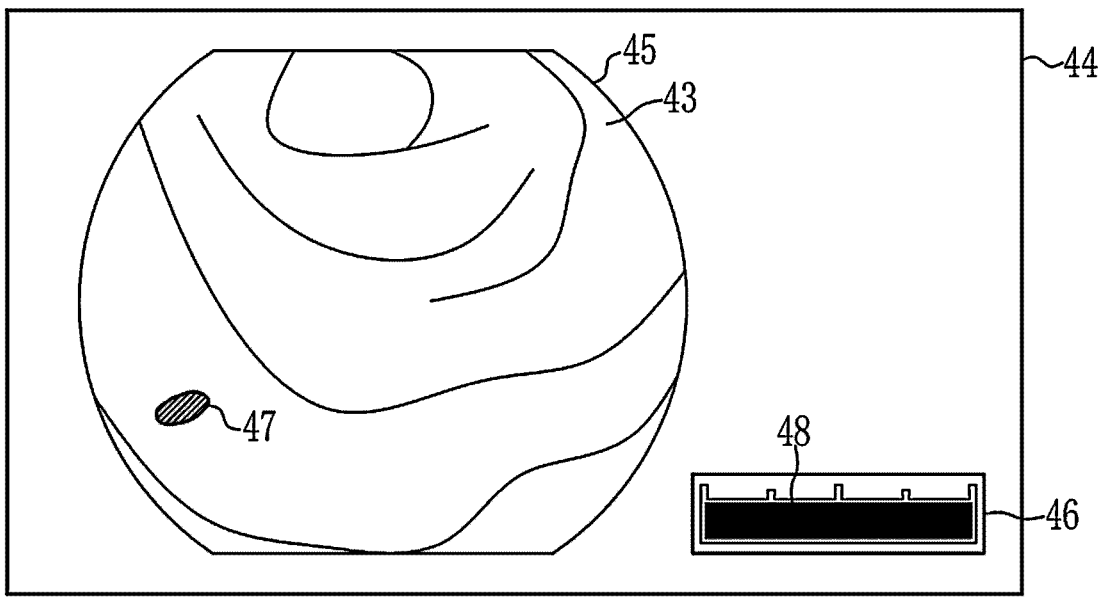
FIG. 5 is an explanatory diagram illustrating a display manner of report information.
Figure 6:
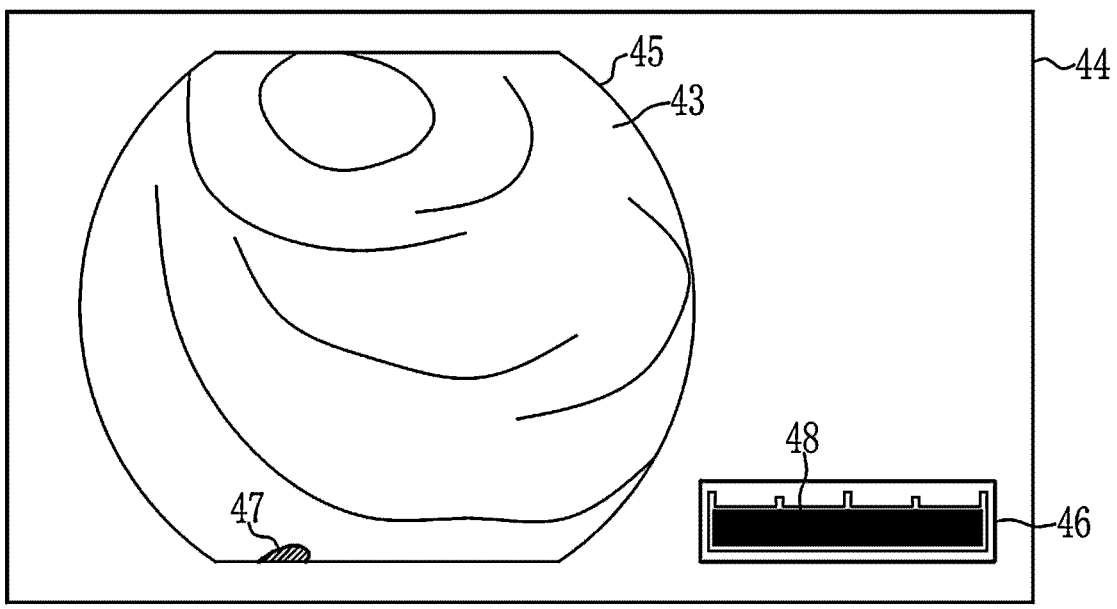
FIG. 6 is an explanatory diagram illustrating a display manner of report information.
Figure 7:
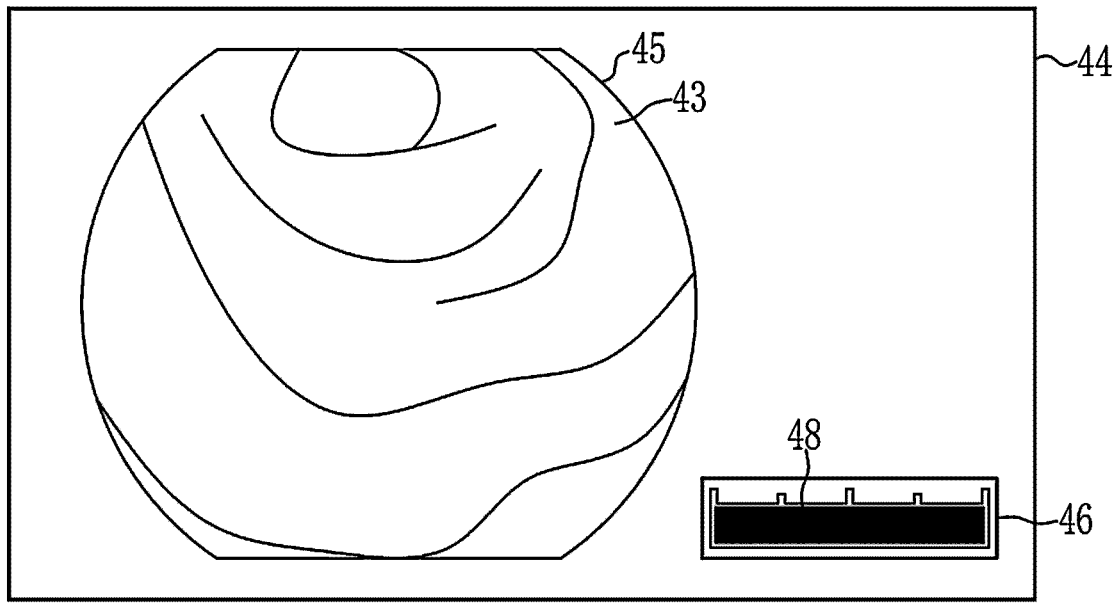
FIG. 7 is an explanatory diagram illustrating a display manner of report information.
Figure 8:
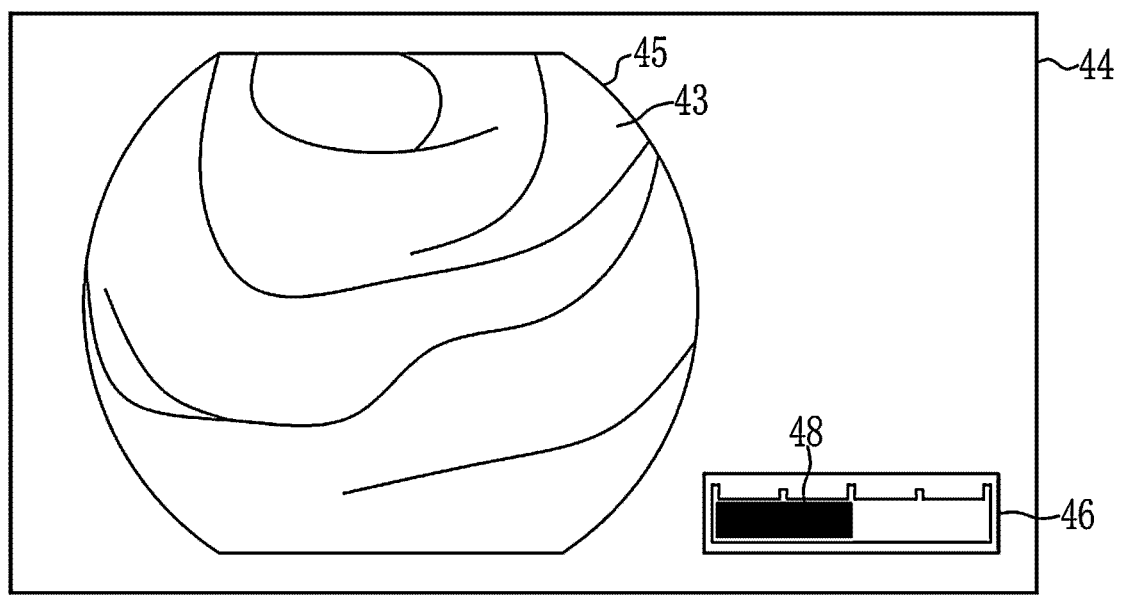
FIG. 8 is an explanatory diagram illustrating a display manner of report information.
Figure 9:
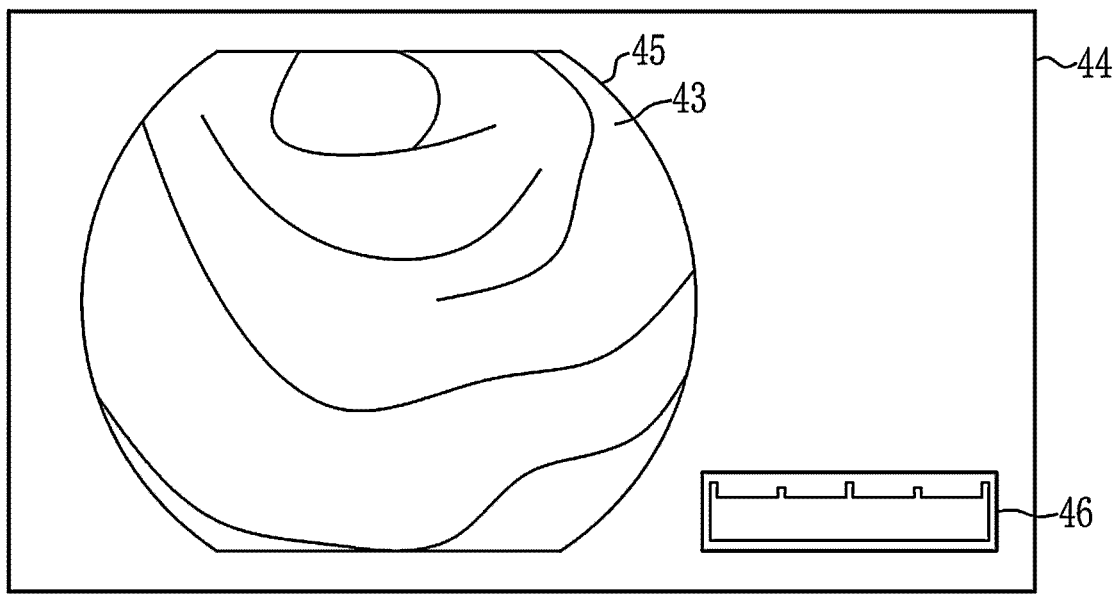
FIG. 9 is an explanatory diagram illustrating a display manner of report information.

As illustrated in FIG. 4 to FIG. 9, in this embodiment, for example, on a display screen 44 (hereinafter also simply referred to as screen) displayed on the display unit 34, a first region 45 for displaying the medical image 43 and a second region 46 for displaying the report information are provided, and the display-manner determining unit 42 determines the display manners of images to be displayed in these first and second regions 45 and 46. Note that FIG. 4 to FIG. 9 illustrate display screens 44 displaying, in screens (in the first region 45), a series of medical images 43 that are sequentially acquired in the order from FIG. 4 to FIG. 9, along with an endoscope examination. Each of FIG. 4, FIG. 5, and FIG. 6 illustrates a detected state in which the region of interest 47 is detected, whereas each of FIG. 7, FIG. 8, and FIG. 9 illustrates an undetected state in which the region of interest 47 is not detected.

In the first region 45 in the detected state, the region of interest 47 is displayed to be superposed on the medical image 43 (see FIG. 4, FIG. 5, and FIG. 6). In addition, in the first region 45 in the undetected state, only the medical image 43 is displayed (see FIG. 7, FIG. 8, and FIG. 9).

Note that the region of interest 47 is displayed to be superposed on the medical image 43 by being hatched (see FIG. 4, FIG. 5, and FIG. 6) in this embodiment. However, the present invention is not limited to this. The region of interest 47 may also be displayed to be superposed on the medical image 43 by being colored. Alternatively, the region of interest 47 may also be displayed to be superposed on the medical image 43 by only the outline thereof being colored for emphasis. In this manner, the display form when displaying the region of interest 47 to be superposed on the medical image 43 can be changed as appropriate. Furthermore, without limitation to the form of displaying the region of interest 47 to be superposed on the medical image 43, for example, the region of interest 47 may be emphasized by, for example, being surrounded by a frame. In addition, since the present invention has a main feature in the display manner of the second region 46 (the display manner of report information), which will be described later, the configuration regarding the first region 45 may be such that only the medical image 43 is displayed without displaying or emphasizing the region of interest 47 even in the detected state. As a matter of course, the configuration may be such that the state in which the region of interest 47 is displayed or emphasized and the state in which only the medical image 43 is displayed without displaying the region of interest 47 is switched by a selecting operation of a user (e.g., a physician performing an endoscopic examination).

In the second region 46 in the detected state, report information indicating that the region of interest 47 is present in the medical image 43 is displayed (see FIG. 4, FIG. 5, and FIG. 6). In this embodiment, the report information is displayed in the form of a bar 48 (time bar). Display of the bar 48 starts in a longest state when the undetected state transitions to the detected state, and display in the longest state is maintained until the detected state transitions to the undetected state. When the detected state transitions to the undetected state, the bar 48 is reduced in length over time (see FIG. 7, FIG. 8, and FIG. 9). That is, in a state where the detected state transitions to the undetected state, the bar 48 that is reduced in length over time is displayed in the second region 46. Note that when a predetermined time elapses after transition to the undetected state, the length of the bar 48 becomes 0, and the bar 48 disappears (becomes no longer displayed, see FIG. 9). In addition, in a case where the undetected state transitions to the detected state before the bar 48 disappears, the length of the bar 48 returns to the longest (see FIG. 4, FIG. 5, and FIG. 6).

In the above manner, by changing the display manner of the second region 46 (the display manner of report information) on the basis of the detection state of the region of interest 47 and the elapsed time after change of the detection state, the user can know whether the detection state is the detected state or the elapsed time after entering the undetected state. Thus, for example, if the region of interest 47 that has become out of the screen is to be returned to the inside of the screen again, it is likely to be intuitively understood how much the endoscope is to be moved back, and the region of interest 47 can be returned to the inside of the screen with ease, reducing the examination load.

Figure 10:
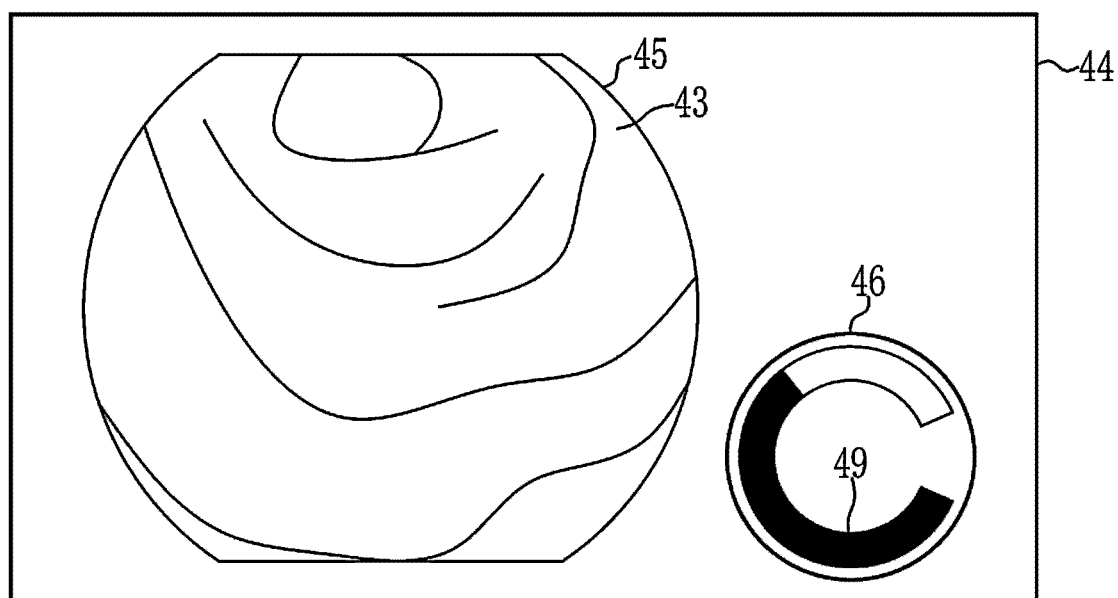
FIG. 10 is an explanatory diagram illustrating a display manner of report information.

Note that the present invention is not limited to the above embodiment, and detailed configurations can be changed as appropriate. For example, although the above embodiment has described an example of indicating the elapsed time by using a linear bar, the elapsed time may alternatively be indicated by using a circular bar 49 as illustrated in FIG. 10.

Figure 11:
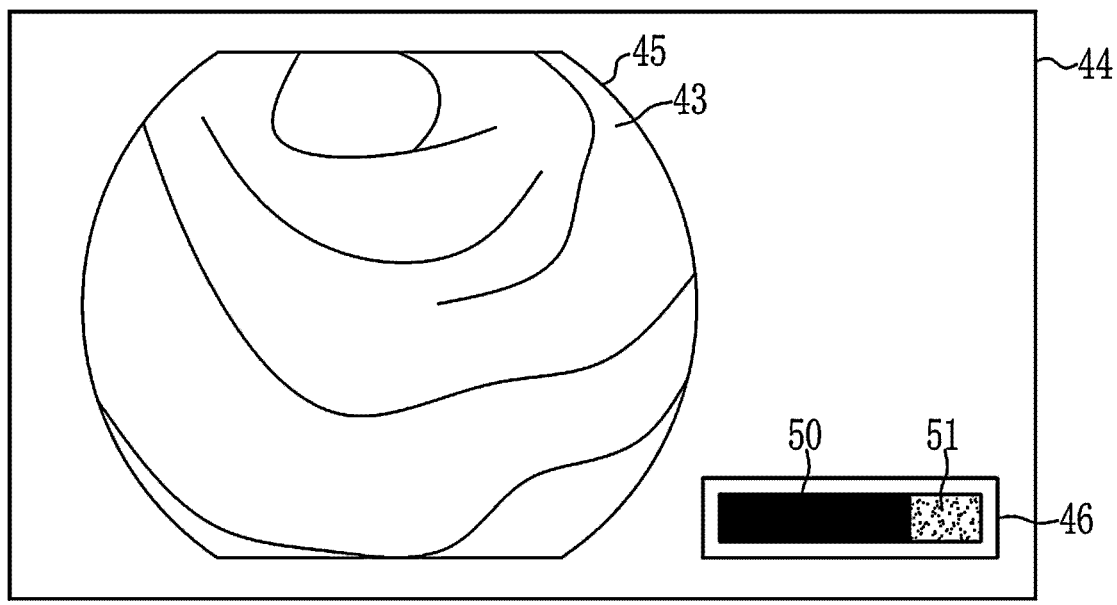
FIG. 11 is an explanatory diagram illustrating a display manner of report information.
Figure 12:
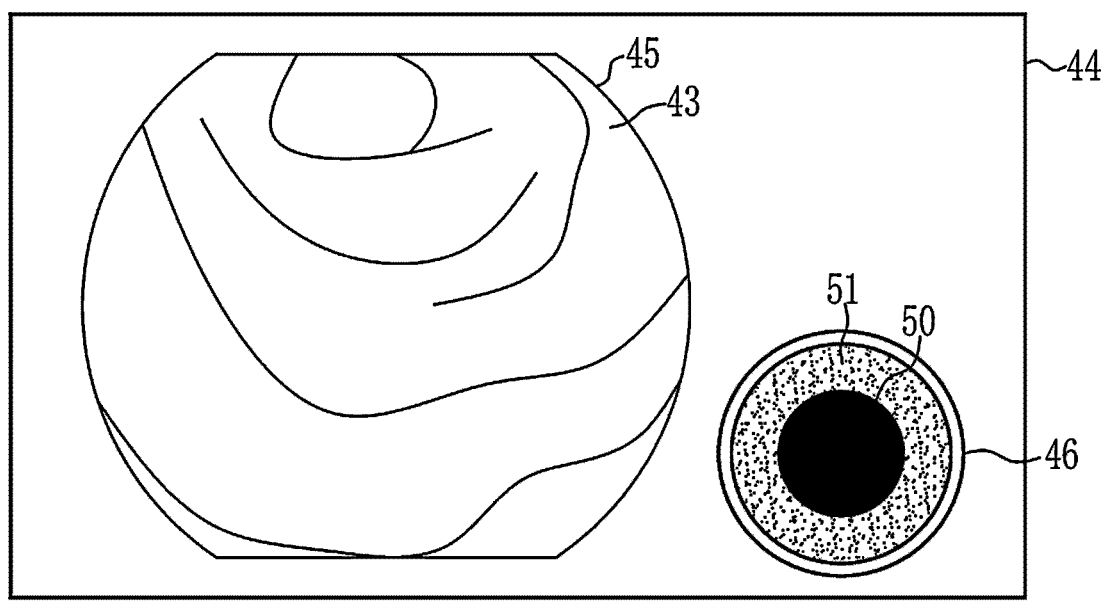
FIG. 12 is an explanatory diagram illustrating a display manner of report information.

In addition, the elapsed time may alternatively be indicated by changing color (display color) as illustrated in FIG. 11 and FIG. 12. In FIG. 11 and FIG. 12, regions 50 and 51 colored in different colors are provided in the second region 46. In the detected state, the entirety of the second region 46 is the region 50. Once the detected state transitions to the undetected state, the region 50 is reduced over time (the length of the region 50 is made shorter in FIG. 11, and the diameter of the region 50 is made smaller in FIG. 12), and, in contrast, the region 51 is increased to indicate the elapsed time. As a matter of course, the elapsed time may also be indicated by changing the density of color (display color) and/or lightness thereof.

Figure 13:
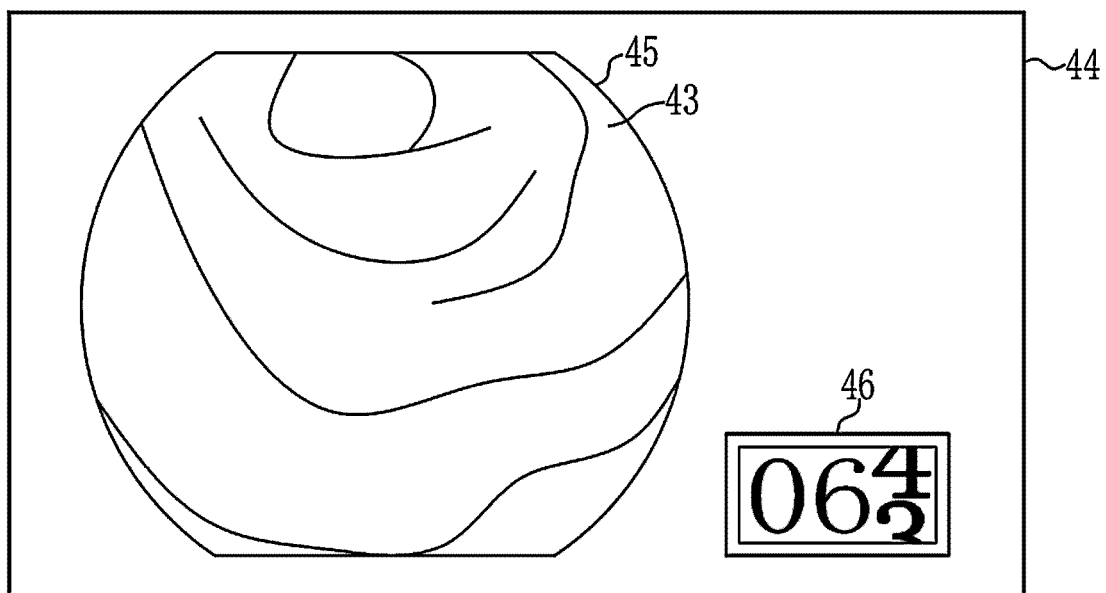
FIG. 13 is an explanatory diagram illustrating a display manner of report information.

Furthermore, as illustrated in FIG. 13, the elapsed time may also be indicated by using a numeral. In FIG. 13, when the detected state transitions to the undetected state, counting down is performed in the second region 46 (the numeric value in the second region 46 is decremented by one per second) to indicate the elapsed time. As a matter of course, the elapsed time may also be indicated by using a character.

Furthermore, the elapsed time may also be indicated by combining a plurality of methods described above, such as indicating the elapsed time by using both the bar and the numeric value.

In addition, although an example of indicating the elapsed time by decreasing the bar and/or the numeric value or the like has been described, the elapsed time may also be indicated by increasing the bar and/or the numeric value or the like.

Note that, in the description with reference to FIG. 10 and subsequent drawings, substantially the same members as those in the above-described embodiment are denoted by substantially the same numerals, and description thereof is omitted.

Figure 14:
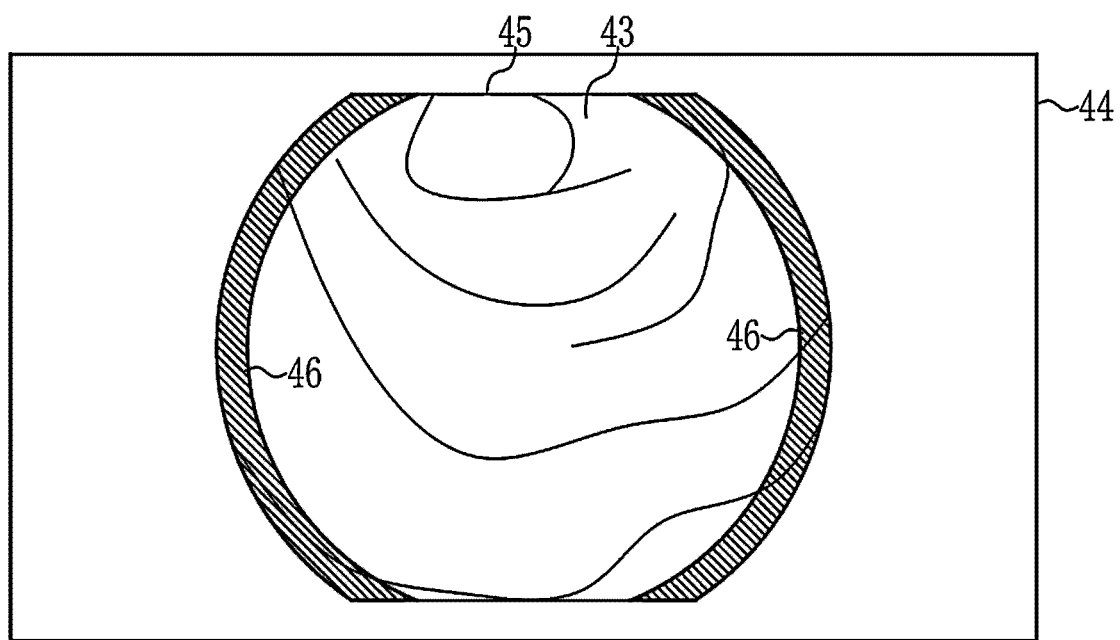
FIG. 14 is an explanatory diagram illustrating a display manner of report information.
Figure 15:
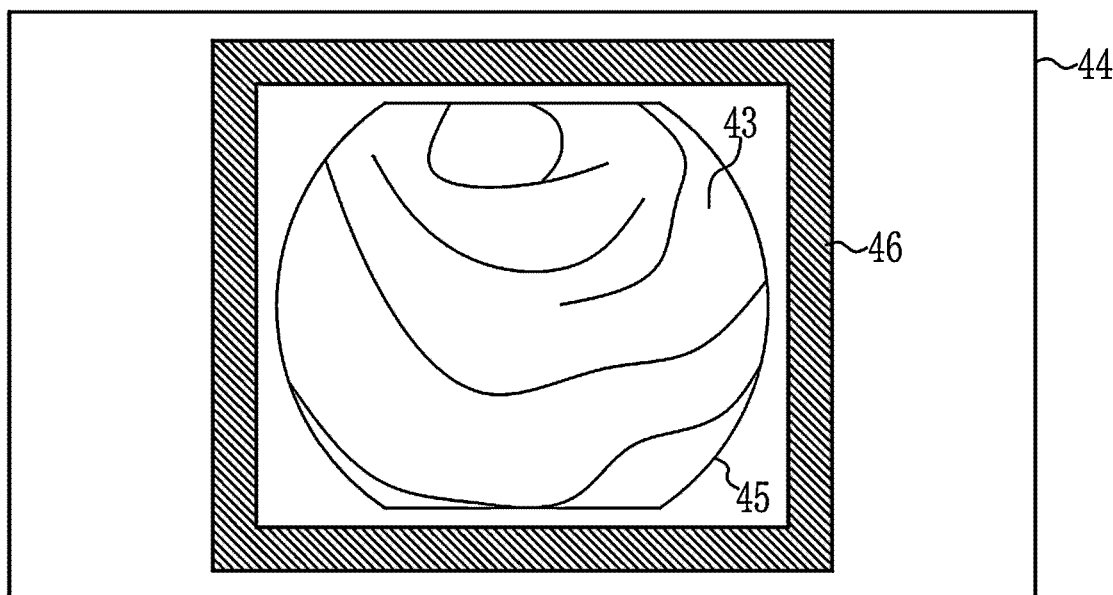
FIG. 15 is an explanatory diagram illustrating a display manner of report information.

In addition, the position and/or shape of the second region 46 can be freely set. Thus, as illustrated in FIG. 14 and FIG. 15, the second region 46 may also be provided on a peripheral part of the first region 45. Note that the peripheral part of the first region 45 may be a region inside the first region 45. In the example in FIG. 14, the second region 46 is inside the first region 45 and in outer edge parts of the first region 45 (the regions illustrated by hatching in FIG. 14). The peripheral part of the first region 45 may also be a region outside the first region 45. In the example in FIG. 15, the second region 46 is a rectangular frame-like region (the region illustrated by hatching in FIG. 15) provided outside the first region 45 so as to surround the first region 45. As a matter of course, the peripheral part of the first region 45 may also be a region across both the region inside the first region 45 and the region outside the first region 45.

Figure 16:
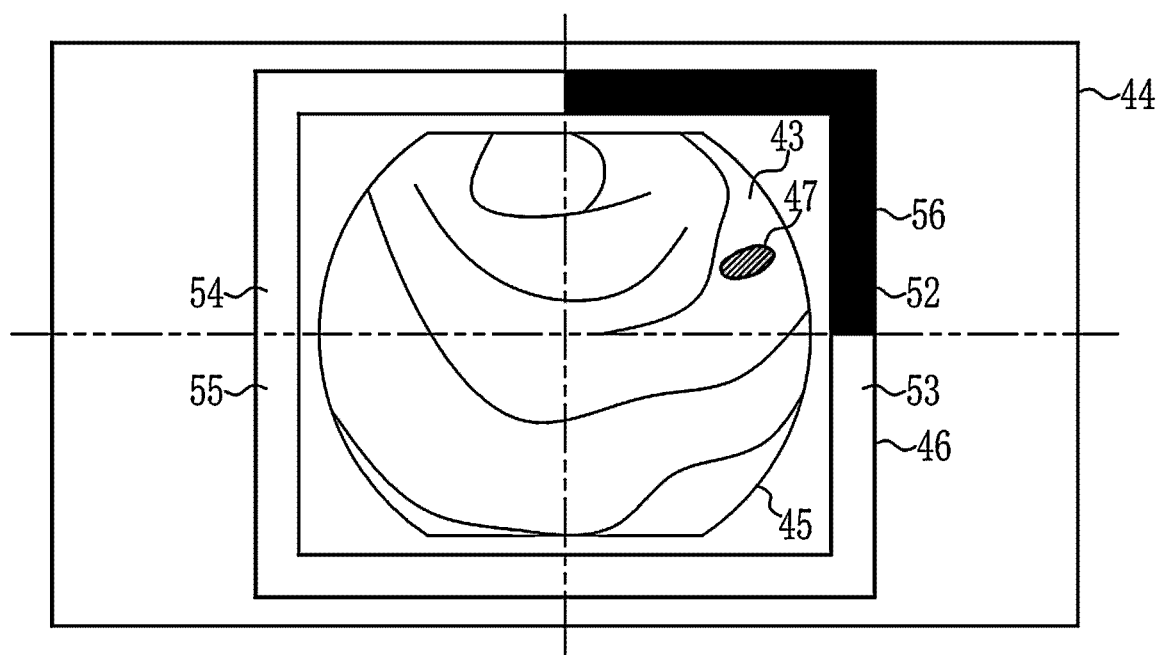
FIG. 16 is an explanatory diagram illustrating a display manner of report information.
Figure 20:
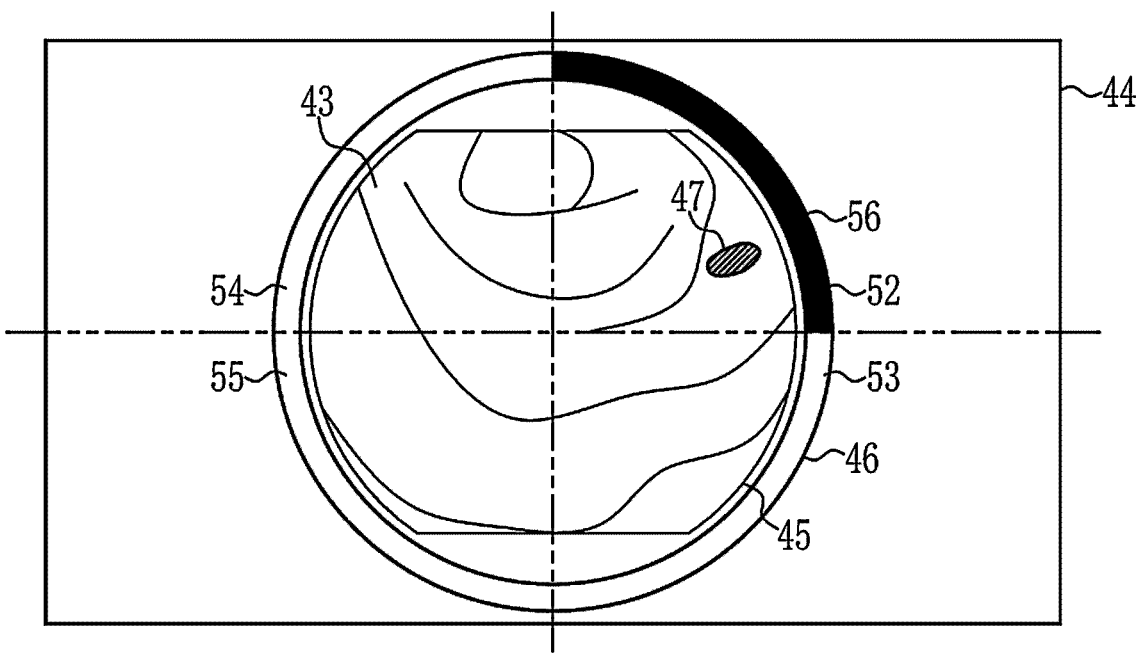
FIG. 20 is an explanatory diagram illustrating a display manner of report information.

Furthermore, the above embodiment has described an example of reporting, by details displayed in the second region 46, that the region of interest 47 has been detected and reporting the elapsed time after the region of interest 47 has no longer been detected. However, the present invention is not limited to this. For example, as illustrated in FIG. 16 and FIG. 20, the detected location of the region of interest 47 may also be reported. In the examples in FIG. 16 and FIG. 20, the second region 46 is provided on the peripheral part of the first region 45, and the detected location of the region of interest 47 is reported by displaying a bar 56 in one of four regions 52 to 55 that are formed by dividing the second region 46 into four regions by using line segments passing through the center of the first region 45.

Specifically, in a case where the undetected state transitions to the detected state, it is checked in which region on the screen among the upper right, the lower right, the upper left, and the lower left, the region of interest 47 has been detected. In a case where the region of interest 47 has been detected in the upper right region on the screen, the bar 56 is displayed in the longest state in the upper right region 52 in the second region 46 on the screen; in a case where the region of interest 47 has been detected in the lower right region on the screen, the bar 56 is displayed in the longest state in the lower right region 53 in the second region 46 on the screen; in a case where the region of interest 47 has been detected in the upper left region on the screen, the bar 56 is displayed in the longest state in the upper left region 54 in the second region 46 on the screen; and in a case where the region of interest 47 has been detected in the lower left region on the screen, the bar 56 is displayed in the longest state in the lower left region 55 in the second region 46 on the screen. Note that FIG. 16 and FIG. 20 illustrate the state in which the region of interest 47 has been detected in the upper right region 52 on the screen and the bar 56 is displayed in the region 52. In addition, in the detected state, the display position (the displayed region) of the bar 56 is moved corresponding to change of the location of the region of interest 47. If the detected state transitions to the undetected state, the display position of the bar 56 is not changed (i.e., the bar 56 is displayed at the position (in the region) corresponding to the most recent detected location of the region of interest 47), and the length of the bar 56 is reduced over time (e.g., the bar 56 is reduced from both ends so that the bar 56 remains in a corner portion of the second region 46). Thus, the location of the region of interest 47 is known with ease in the detected state. In addition, the detected location of the region of interest 47 at the last detection is known even in the undetected state. This makes it easier to return the region of interest 47 to the inside of the screen, further reducing the examination load.

Figure 17:
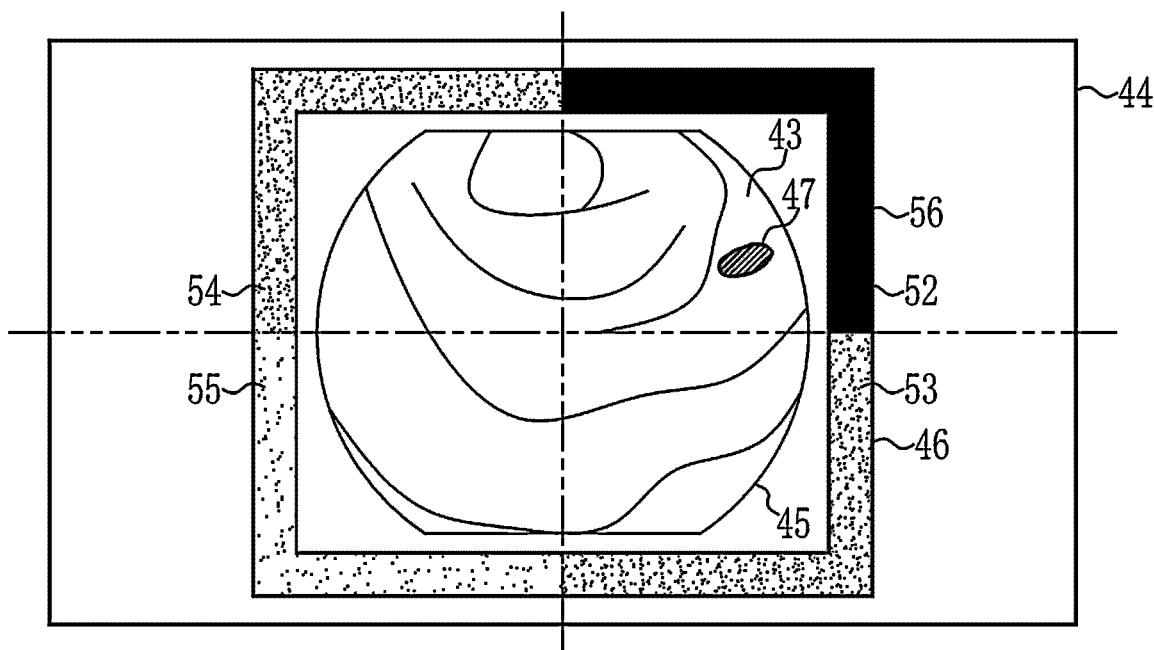
FIG. 17 is an explanatory diagram illustrating a display manner of report information.

Note that the display manner of the second region 46 for reporting the detected location of the region of interest 47 is not limited to this. For example, in the above-described examples in FIG. 16 and FIG. 20, examples of changing the display position of the bar 56 within the second region 46 depending on the location of the region of interest 47 has been described. However, the display position and/or the shape of the second region 46 itself may also be changed depending on the location of the region of interest 47. In addition, as illustrated in FIG. 17, information about the region of interest 47 may also be displayed for a region in the second region 46, the region being different from the detected location of the region of interest 47. In the example in FIG. 17, for example, the region 52 corresponding to the detected location of the region of interest 47 is colored in blue, the region 55 that is the most distant from the detected location of the region of interest 47 (the region 55 not adjacent to the region corresponding to the detected location of the region of interest 47) is colored in red, and the regions 53 and 54 adjacent to the region corresponding to the detected location of the region of interest 47 are colored in yellow. Thus, for example, even in a case where an examination is being performed with attention to the peripheral part of the region 55 that is the most distant from the region of interest 47, it is known that the region of interest 47 has been detected, preventing an issue of failing to notice the region of interest 47.

In addition, the above embodiment has described an example of reporting both that the region of interest 47 has been detected and the elapsed time after the region of interest 47 has no longer been detected. However, the configuration may be such as to report only the elapsed time after the region of interest 47 has no longer been detected. In this case, even in a case where the undetected state transitions to the detected state, the elapsed time after entering the undetected state may be reported by displaying, for example, the bar 48 described in the above embodiment when the detected state transitions to the undetected state, without display in the second region 46 (see FIG. 7 to FIG. 9).

Figure 18:
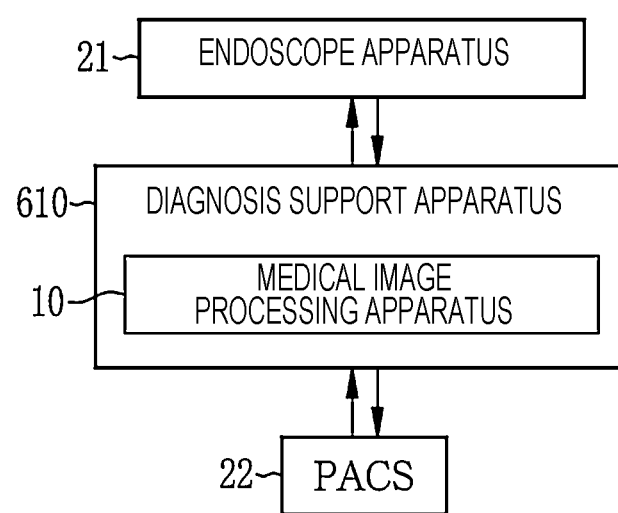
FIG. 18 is a diagnosis support apparatus including the medical image processing apparatus.
Figure 19:
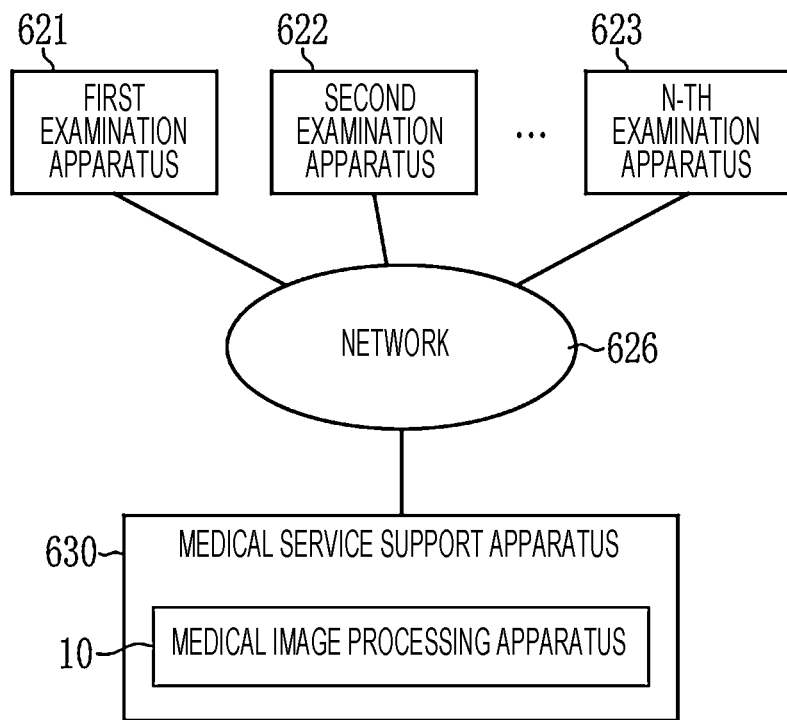
FIG. 19 is a medical service support apparatus including the medical image processing apparatus.

Note that as illustrated in FIG. 18, the medical image processing apparatus 10 according to the above embodiment or other modifications may be included in a diagnosis support apparatus 610 using the endoscope apparatus 21 or other modalities and the PACS 22 in combination. In addition, as illustrated in FIG. 19, the medical image processing apparatus 10 according to the above embodiment or other modifications may be included in a medical service support apparatus 630 that establishes connection with various examination apparatuses via any network 626. The various examination apparatuses are, for example, a first examination apparatus 621, a second examination apparatus 622, . . . , an N-th examination apparatus 623, and the like, each including the endoscope apparatus 21.

Besides, the medical image processing apparatus 10, the endoscope apparatus 21, and various apparatuses or systems including the medical image processing apparatus 10 can be used by making the following various changes, for example.

As the medical image, an ordinary-light image may be used. The ordinary-light image is obtained by radiating light of a white range or light of a plurality of wavelength ranges as the light of the white range.

In a case where an image obtained by radiating the light of the particular wavelength range is used as the medical image, as the particular wavelength range, a range narrower than the white wavelength range may be used.

The particular wavelength range is, for example, a visible wavelength range of blue or green.

In a case where the particular wavelength range is the visible wavelength range of blue or green, the particular wavelength range preferably includes a wavelength range that is greater than or equal to 390 nm and is less than or equal to 450 nm, or is greater than or equal to 530 nm and is less than or equal to 550 nm, and the light of the particular wavelength range preferably has a peak wavelength in the wavelength range that is greater than or equal to 390 nm and is less than or equal to 450 nm, or is greater than or equal to 530 nm and is less than or equal to 550 nm.

The particular wavelength range is, for example, a visible wavelength range of red.

In a case where the particular wavelength range is the visible wavelength range of red, the particular wavelength range preferably includes a wavelength range that is greater than or equal to 585 nm and is less than or equal to 615 nm, or is greater than or equal to 610 nm and is less than or equal to 730 nm, and the light of the particular wavelength range preferably has a peak wavelength in the wavelength range that is greater than or equal to 585 nm and is less than or equal to 615 nm, or is greater than or equal to 610 nm and is less than or equal to 730 nm.

The particular wavelength range may include, for example, a wavelength range in which a light absorption coefficient differs between oxyhemoglobin and deoxyhemoglobin, and the light of the particular wavelength range may have a peak wavelength in the wavelength range in which the light absorption coefficient differs between oxyhemoglobin and deoxyhemoglobin.

In a case where the particular wavelength range includes the wavelength range in which the light absorption coefficient differs between oxyhemoglobin and deoxyhemoglobin, and the light of the particular wavelength range has the peak wavelength in the wavelength range in which the light absorption coefficient differs between oxyhemoglobin and deoxyhemoglobin, the particular wavelength range preferably includes a wavelength range of 400±10 nm, 440±10 nm, or 470±10 nm, or a wavelength range that is greater than or equal to 600 nm and is less than or equal to 750 nm, and the light of the particular wavelength range preferably has a peak wavelength in the wavelength range of 400±10 nm, 440±10 nm, or 470±10 nm, or in the wavelength range that is greater than or equal to 600 nm and is less than or equal to 750 nm.

In a case where the medical image is an inside body image of an inside of a body, the inside body image may have information of fluorescent light emitted by a fluorescence substance in the body.

In addition, as the fluorescent light, fluorescent light obtained by irradiating the inside of the body with excitation light having a peak wavelength that is greater than or equal to 390 nm and is less than or equal to 470 nm may be used.

In a case where the medical image is an inside body image of an inside of a body, as the above-described particular wavelength range, a wavelength range of infrared light may be used.

In a case where the medical image is an inside body image of an inside of a body and the wavelength range of infrared light is used as the above-described particular wavelength range, the particular wavelength range preferably includes a wavelength range that is greater than or equal to 790 nm and is less than or equal to 820 nm, or is greater than or equal to 905 nm and is less than or equal to 970 nm, and the light of the particular wavelength range preferably has a peak wavelength in the wavelength range that is greater than or equal to 790 nm and is less than or equal to 820 nm, or is greater than or equal to 905 nm and is less than or equal to 970 nm.

The medical image acquiring unit 11 may include a special-light-image acquiring unit that acquires a special-light image having a signal in a particular wavelength range on the basis of the ordinary-light image obtained by radiating the light of the white range or by radiating light of a plurality of wavelength ranges as the light of the white range. In this case, the special-light image may be used as the medical image.

The signal in the particular wavelength range may be obtained through a calculation based on color information of RGB or CMY included in the ordinary-light image.

A feature-quantity-image generation unit may be included. The feature-quantity-image generation unit generates a feature-quantity image through a calculation based on at least one of the ordinary-light image that is obtained by radiating the light of the white range or light of a plurality of wavelength ranges as the light of the white range or the special-light image obtained by radiating the light of the particular wavelength range. In this case, the feature-quantity image may be used as the medical image.

Regarding the endoscope apparatus 21, a capsule endoscope may be used as the endoscope 31. In this case, the light source device 32 and part of the processor device 33 may be installed on the capsule endoscope.

In the above embodiment and modifications, a hardware structure of processing units that perform various kinds of processing, such as the medical image acquiring unit 11, the medical image analysis processing unit 12, each unit constituting the medical image analysis processing unit 12, the display control unit 15, the input receiving unit 16, the general control unit 17, the medical image acquiring unit 35, the medical image analysis processing unit 36, the display control unit 37, the region-of-interest detecting unit 41, and the display-manner determining unit 42 is any of the following various processors. Various processors include a central processing unit (CPU) and a graphical processing unit (GPU) that are general-purpose processors functioning as various processing units by executing software (programs), a programmable logic device (PLD) that is a processor in which the circuit configuration is changeable after manufacture, such as field programmable gate array (FPGA), a dedicated electric circuit that is a processor having a circuit configuration that is specially designed to execute various kinds of processing, and the like.

One processing unit may be constituted by one of these various processors, or may be constituted by two or more processors of the same type or different types in combination (e.g., a combination of a plurality of FPGAs, a combination of a CPU and an FPGA, or a combination of a CPU and a GPU). In addition, a plurality of processing units may be constituted by one processor. As a first example for constituting a plurality of processing units with one processor, one processor may be constituted by a combination of one or more CPUs and software, and this processor may function as a plurality of processing units, as typified by a computer such as a client or a server. As a second example, a processor may be used that implements the functions of the entire system including a plurality of processing units with one integrated circuit (IC) chip, as typified by a system on chip (SoC) or the like. In this manner, various processing units are constituted by one or more of the above various processors in terms of hardware structure.

More specifically, the hardware structure of these various processors is electric circuitry constituted by combining circuit elements such as semiconductor elements.

REFERENCE SIGNS LIST 10 medical image processing apparatus
11 medical image acquiring unit
12 medical image analysis processing unit
13 display unit
15 display control unit
16 input receiving unit
17 general control unit
18 storage unit
21 endoscope apparatus
22 picture archiving and communication system (PACS)
31 endoscope
32 light source device
33 processor device
34 display unit
35 medical image acquiring unit
36 medical image analysis processing unit
37 display control unit
41 region-of-interest detecting unit
42 display-manner determining unit
43 medical image
44 display screen
45 first region
46 second region
47 region of interest
48 bar
49 bar
50,51 region
52 to 55 region
56 bar
610 diagnosis support apparatus
621 first examination apparatus
622 second examination apparatus
626 network
630 medical service support apparatus
633 examination apparatus

What is claimed is:

1. A medical image processing apparatus comprising:
a processor configured to function as:
a medical image acquiring unit that acquires a medical image obtained by capturing an image of an observation target;
a region-of-interest detecting unit that detects a region of interest from the medical image; and
a display control unit that causes a display to display report information and the medical image, the report information reporting that the region of interest has been detected,
wherein the display control unit causes the display to display the report information when a detection state of the region of interest is a detected state in which the region of interest is detected,
wherein, by referring to an elapsed time after the detection state of the region of interest has transitioned from the detected state to an undetected state in which the region of interest is not detected, the display control unit changes the display manner of the report information in the undetected state, and
wherein, in an undetected state in which the region of interest is not detected, the display control unit indicates a most recent detected location of the region of interest by the display manner of the report information, wherein a region in which the report information is displayed is provided to surround the displayed medical image, and is divided into a plurality of subregions, and wherein the report information is displayed in one of the subregions which corresponds to the most recent detected location.

2. The medical image processing apparatus according to claim 1, wherein, if the detection state of the region of interest transitions from an undetected state in which the region of interest is not detected to a detected state in which the region of interest is detected, the display control unit causes the display to display the report information in a first display manner, and, if the detection state of the region of interest transitions from the detected state to the undetected state, the display control unit causes the display to display the report information in a second display manner.

3. The medical image processing apparatus according to claim 1, wherein, while the detection state of the region of interest is a detected state in which the region of interest is detected, the region of interest is displayed to be superposed on the medical image.

4. The medical image processing apparatus according to claim 1, wherein the report information is displayed in a form of a circular or linear time bar that changes in length in accordance with the elapsed time.

5. The medical image processing apparatus according to claim 1, wherein the report information is displayed in a form of a character or a numeral indicative of the elapsed time.

6. The medical image processing apparatus according to claim 1, wherein the report information is displayed in a form of changing a hue or a density in accordance with the elapsed time.

7. The medical image processing apparatus according to claim 1, wherein, in a screen of the display, a first region displaying the medical image and a second region displaying the report information are provided.

8. The medical image processing apparatus according to claim 7, wherein the second region is provided in a peripheral part of the first region.

9. The medical image processing apparatus according to claim 1, wherein, in a detected state in which the region of interest is detected, the display control unit indicates a detected location of the region of interest in the medical image by the display manner of the report information.

10. The medical image processing apparatus according to claim 9, wherein the display control unit indicates the detected location by a display position of the report information.

11. The medical image processing apparatus according to claim 1, wherein the display control unit causes the display to display the elapsed time as the report information, the elapsed time being a time after the detection state of the region of interest has transitioned from the detected state to the undetected state.

* * * * *